United States Patent [19]

Sturm et al.

[11] 4,002,461
[45] Jan. 11, 1977

[54] SUBSTITUTED 2-AZABICYCLOALKANES AS SELECTIVE HERBICIDES

[75] Inventors: Elmar Sturm, Aesch; Christian Vogel, Binningen, both of Switzerland

[73] Assignee: Ciba-Geigy Corporation, Ardsley, N.Y.

[22] Filed: Nov. 7, 1975

[21] Appl. No.: 630,057

Related U.S. Application Data

[60] Division of Ser. No. 417,303, Nov. 19, 1973, Pat. No. 3,936,458, which is a continuation-in-part of Ser. No. 52,986, July 7, 1970, abandoned.

[30] Foreign Application Priority Data

July 16, 1969 Switzerland ............... 10833/69
June 11, 1970 Switzerland ............... 8773/70

[52] U.S. Cl. .................................. 71/94; 71/67; 71/92; 71/93
[51] Int. Cl.² ................................... A01N 9/22
[58] Field of Search ......................... 71/94

[56] References Cited

UNITED STATES PATENTS 3,639,404  2/1972  Richter et al. ............... 71/94 X
3,776,912  12/1973  Sturm et al. ............... 71/94 X Primary Examiner—Joseph P. Brust
Attorney, Agent, or Firm—Harry Falber

[57] ABSTRACT

Compounds of the Formula I

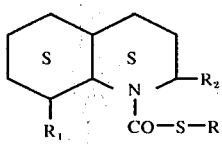

wherein R represents alkyl having from 1 to 4 carbon atoms and one of the symbols $R_1$ and $R_2$ is methyl and the other is hydrogen possess favorable herbicidal properties for practical purposes when used in crops for controlling their infestation by undesired plant growth.

6 Claims, No Drawings

SUBSTITUTED 2-AZABICYCLOALKANES AS SELECTIVE HERBICIDES

CROSS REFERENCE

This is a divisional of application Ser. No. 417,303, filed on Nov. 19, 1973, now U.S. Pat. No. 3,936,458 which, in turn, is a continuation-in-part of application Ser. No. 52,986, filed July 7, 1970, now abandoned.

The present invention concerns substituted 2-azabicycloalkanes, process for their production, furthermore selective herbicidal compositions which contain such substituted 2-azabicycloalkanes and methods for the control of weeds and wild grasses employing the new active substances or the compositions containing them.

The expression "substituted 2-azabicycloalkanes" is used here and in the following to designate substituted methyl-2-azabicyclo-(4.4.0)-decanes which also may called decahydro-quinolines.

The new substituted 2-azabicycloalkanes are 1-alkylthio-carbonyl-(2-or 8-methyl) decahydroquinolines and correspond to the Formula I

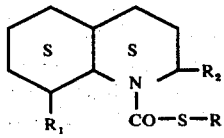

wherein

R represents alkyl having from 1 to 4 carbon atoms, one of the symbols $R_1$ and $R_2$ is methyl and the other is hydrogen.

Alkyl groups R are straight or branched chain alkyl groups such as the methyl, ethyl, n-propyl, isopropyl, n-butyl, isobutyl, sec-butyl and tert-butyl groups. Compounds wherein R represents the n-propyl group are preferred.

The substituted 2-azabicycloalkanes of Formula I are obtained by reacting a 2-azabicycloalkane of the Formula II

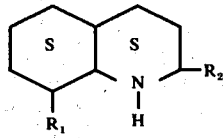

either with a thiocarbonyl halide of the Formula III

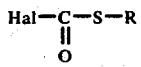

or with the individual components of such a thiocarbonyl halide, namely phosgene and an alkali metal salt of a mercaptan of the Formula IV

 (IV)

in the presence of an acid-binding agent. In the Formulas II–IV, R, $R_1$ and $R_2$ have the meanings given for Formula I and Hal in Formula III designates chlorine or bromine. It is advisable to perform the reactions in a solvent and/or diluting agent which is inert towards the reaction components. The type of dispersing agent to be used is largely determined by the acidbinding agent employed. If organic bases, such as tertiary amines, are used, it is advisable to also use an organic solvent. When inorganic bases are used, water and aqueous mixtures of water-miscible organic solvents are suitable. In general, the following tertiary amines can serve as acid-binding agents: pyridine and pyridine bases, triethyl amine etc.; likewise, the 2-azabicycloalkanes of Formula II which are used may be employed in excess and thus serve as acid-binding agent. Suitable inorganic bases are the hydroxides and carbonates of alkali and alkaline earth metals, primarily sodium hydroxide, sodium carbonate, potassium carbonate, furthermore the hydroxides and carbonates of lithium, barium, strontium and magnesium as well as quaternary ammonium compounds which react in the presence of water as bases, for example tetramethyl ammonium hydroxide, etc.

The following may be used as solvents: aliphatic and aromatic hydrocarbons and halogenohydrocarbons such as benzene, toluene, xylene, petroleum ether, chlorobenzene, methylene chloride, chloroform, carbontetrachloride, ether and ether-type solvents such as dialkyl ether and tetrahydrofuran; suitable as water-miscible solvents ate: alkanols, ketones, etc.

In the reaction of a 2-azabicycloalkane of Formula II with phosgene and analkali metal salt of a mercaptan, the 2-azabicycloalkane-2-carbonyl halide obtained as intermediate can be reacted without further purification with an alkali metal salt of a mercaptan of Formula IV.

According to another process of the present invention, the new substituted 2-azabicycloalkanes of Formula I are obtained by reacting a 2-azabicycloalkane of Formula II in the presence of an acid-binding agent with carbon oxysulfide (COS) and subsequently with an alkylating agent. suitable acid-binding agents are those listed above, preferably alkali metal hydroxides. Suitable alkylating agents are primarily alkyl halides, furthermore dialkyl sulfuric acid esters and alkyl esters of toluene sulfonic acids.

The reactions according to the invention of a substituted 2-azabicycloalkane of Formula II with a thiocarbonyl halide of Formula III or its individual components, are performed at temperatures of from −20° to 100° C, preferably between 0° and 30° C, those with carbon oxysulfide and alkylating agents between −20° and 100° C, preferably between 0° and 30° C.

The 2-azabicycloalkanes of Formula II are known. They are prepared in a manner known per se by hydrogenation of the corresponding heteroaromatic compounds at temperatures of from 100° to 180° C, and of from 100 to 200 atmospheres of excess pressure, in aqueous emulsions and in the presence of ruthenium/-carbon catalysts.

The starting compounds encompassed by Formula II exist in two isomeric forms, i.e. in the cis and the trans configuration, which lead to two series of compounds of Formula I having also the cis or trans configuration and differing in their herbicidal properties. If mixtures of the cis- and the transform of a distinct 2-azabicycloalkane according to Formula II are used also cis/trans mixtures of the compounds of Formula I are obtained.

The new substituted 2-azabicycloalkanes of Formula I have excellent herbicidal properties. Some are suitable as general herbicides and some are suitable for the control of weeds and wild grasses in rice plantations (water and dry cultivations). 2-Azabicycloalkanes of Formula I, wherein R is ethyl, n-propyl or isopropyl have particularly good herbicidal properties. These active substances are effective against weeds which are difficult to control in rice plantations: for example Echinochloa sp., Eleocharis sp., Panicum sp., Cyperaceae, Paspalum sp. etc. in water cultivations; and in dry cultivations again Echinochloa sp., Digitaria sp., Brachiaria sp., Sida sp., Cyperaceae, Acanthosperum sp. etc. Since the active substances only gradually destroy the plants and thus do not drastically disturb the oxygen balance and the biological balance, they are well suited for use in water cultivations. Furthermore, the active substances have broad range of effectiveness against a large variety of aquatic weeds, e.g. against emersed plants, aquatic plants with and without floating leaves, submersed plants, algae etc.

The broad range of action of the new substituted 2-azabicycloalkanes of Formula I makes it possible to employ them in the important control of weeds and wild grasses in the areas surrounding the rice plantations such as ditches, beds of canals, dams etc. These active substances destroy not only the wild grasses named, which grow in rice fields, but also other grass-type and broad-leafed weeds. The active substances can also be applied in the preparation of the rice beds, and after the emergence of the plants for the destruction of weeds which are already standing. In both water cultivations as well as in dry cultivations, the rice is not damaged by application of the new substituted 2-azabicycloalkanes in the usual application amounts, in higher amounts most of the damage caused is reversible. This application amounts vary and depend upon the time of application; they lie between 0.5 and 6, preferably 4 kg of active substance per hectare, by preemergence application. Application amounts of from 10 to 30 kg of active substance per hectare are used for total destruction of all of the standing weeds, for instance on fallow ground adjacent to the cultivated field as well as for the determination of the general herbicidal activity. The use of the new active substances is not detrimental to crop rotation which is important in the cultivation of rice.

In addition such substituted 2-azabicycloalkanes can also be employed as growth regulators, e.g. for defoliation, delay of blossoming, etc.; some of them stimulate the vegetative storage organelles, in some case simultaneously decreasing the length of growth.

Herbicidal polymethyleneimino thiocarbamates and azabicyclononanes have been described in U.S. Pat. Nos. 3,198,786 and 3,344,134; although they have a good selectivity on rice, their effect on wild grasses is slight and dicotyl weeds are not damaged. The active substances of Formula I according to the invention show, with equally good selectivity on rice, much better effectiveness against wild grasses and have a much better range of effectiveness against dicotyl weeds. Some of them, while being well tolerated by wheat, soya beans and cotton, are herbicidally effective against a large number of grass-type weeds against which the above named comparative compounds show no effect, even when applied in very low concentrations (i.e. amount of application).

Compounds of a general formula which covers also substituted 2-azabicycloalkanes of Formula I of this invention have been disclosed in U.S. Pat. No. 3,639,404, but none of the superior compounds specifically mentioned herein has been described earlier.

To produce herbicidal compositions the active substances are mixed with suitable carriers and/or distributing agents. To broaden the range of action, other herbicides may be admixed with these agents, for example from the triazine series such as halogenodiamino-s-triazines, and alkoxy- and alkylthiodiamino-s-triazines, triazoles, diazines such as uracils, aliphatic carboxylic and halogenocarboxylic acids, halogenated benzoic acids and phenylacetic acids, aryloxyalkane carboxylic acids, hydrazides, amides, nitriles, esters of such carboxylic acids, carbamic and thiocarbamic acid esters, ureas, etc.

The following non-limitative examples illustrate the process for the production of the new substituted 2--azabicycloalkanes of Formula I. Where not expressly stated otherwise, temperatures are given in degrees Centigrade.

EXAMPLE 1

109 g of decahydro-quinaldine are dissolved in 750 ml of benzene and 72 g of triethylamine are added to this solution. To this mixture 88 g of ethyl chlorothioformiate are added dropwise. The reaction mixture is stirred for 5 hours at room temperature, the precipitated triethylammonium chloride is filtered off and washed with benzene; the filtrate is evaporated in vacuum. The yellowish oil obtained is distilled in vacuum and 115 g of 1-(ethylthio-carbonyl)-2-methyl-decahydro-quinoline are obtained as a colorless oil, b.p. 108°–120°/0.02 Torr.

EXAMPLE 2

A mixture of 15 g decahydro-quinaldine dissolved in 200 ml of diethylether and 4 g of sodium hydroxide in 50 ml of water is reacted while stirring and cooling at −5° to 0° with 10 g of phosgene. An ethereal solution of 1-chlorocarbonyl-2-methyl-decahydro-quinoline is obtained. When an aqueous solution of 8.4 g of sodium ethylmercaptide is added to the ethereal solution at room temperature with stirring, 16 g of an almost colorless oil are obtained. The physical constants of this oil coincide with those of the compound of Example 1.

EXAMPLE 3

6.5 g of carbon oxysulfide are bubbled at 0° to 5° while stirring into a solution of 15 g of decahydro-quinaldine and 4 g of sodium hydroxide in 200 ml of 50% by weight aqueous ethanol. After 1 hour the mixture is heated to 20°–25° and 13.7 g of n-butylbromide are added all at once. The reaction mixture is stirred for 10 hours at room temperature and the ethanol is evaporated in vacuum. The residual oil is dissolved in methylene chloride and the solvent is removed. The residual oil is distilled in vacuum and 14 g of 1-(n-butylthio-carbonyl)-2-methyl-decahydro-quinoline are obtained as colorless oil, b.p. 125°–127°/0.01 Torr.

EXAMPLE 4

A solution of 3.2 g of sodium hydroxide in 50 ml of water is added, while stirring, to a solution of 12.2 g of 8-methyldecahydro-quinoline in 150 ml of diethylether. To this mixture, 11.1 g of isopropyl chlorothioformiate are added dropwise with vigorous stirring and cooling at 0° to 5°. Stirring is continued for 12 hours at room temperature, the phases are separated the ethereal phase is washed neutral and the ether is evaporated. The brownish oil obtained is distilled in vacuum and 51 g of 1-(isopropylthio-carbonyl)-8-methyl-decahydro-quinoline are obtained as a colorless oil, b.p. 104°–106°/0.01 Torr.

Following the procedures given in these examples, using the corresponding amounts of 2-azabicycloalkane of Formula II and thiocarbonyl halide of Formula III (or the corresponding carbon oxysulfide and alkylating agent), the compounds of Formula I listed in the following table are produced:

Table I

| Example No. | Compound | boiling point or index of refraction |
|---|---|---|
| 5 | 1-(methylthio-carbonyl)-2-methyl-deca-hydroquinoline | 97–100°/0.005 Torr |
| 6 | 1-(n-propylthio-carbonyl)-2-methyl-decahydroquinoline | $n_D^{20} = 1.5265$ |
| 7 | 1-(isopropylthio-carbonyl)-2-methyl-decahydroquinoline | 96 – 98°/0.01 Torr |
| 8 | 1-(sec.butylthio-carbonyl)-2-methyl-decahydroquinoline | 118–122°/0.01 Torr |
| 9 | 1-(methylthio-carbonyl)-8-methyl-deca-hydroquinoline | 82–84°/0.01 Torr |
| 10 | 1-(ethylthio-carbonyl)-8-methyl-deca-hydroquinoline | 97–100°/0.01 Torr |
| 11 | 1-(n-propylthio-carbonyl)-8-methyl-decahydroquinoline | 103–110°/0.01 Torr |
| 12 | 1-(n-butylthio-carbonyl)-8-methyl-deca-hydroquinoline | 120–125°/0.01 Torr |

Selective preemergence test with test plants grown from seed

Directly after sowing the test plants in seed trays, the active substances are applied to the surface of the soil as aqueous suspension, obtained from a 25 % wettable powder. The seed trays are then kept in daylight at 22°–25° and 50 – 70% relative humidity.

They were evaluated after 28 days according to the scale/mentioned under I. The following test plants were sown:

| | |
|---|---|
| rice, dry | (Oryza oryzoides) |
| rice, in water | |
| wheat | (Triticum vulgare) |
| soyabean | (Glycine hyspida) |
| cotton | (Gossypium herbaccara) |
| Italian Raygrass | (Lolium perenne) |
| millet | (Setaria italica) |
| millet in rice, dry | (Echinochloa crus galli) |
| millet in rice, in water | |
| common meadow grass | (Poa trivialis) |
| field foxtail | (Alopecurus myosuroides) |
| large crabgrass | (Digitaria sanguinalis) |
| pigweed | (Amaranthus docendens) |

The production of herbicidal compositions according to the invention is performed in a known manner by intimate mixing and grinding of active substances of the general Formula I together with suitable carriers, optionally with the addition of dispersing agents or solvents, which are inert towards the active substances. The active substances can be used and applied as: dusts, scattering agents, granulates, coated granulates, impregnated granulates, homogeneous granulates, wettable powders, pastes, emulsions or solutions.

For the production of solid preparations (dusts, scattering agents, granulates) the active ingredients are mixed with solid carriers. Examples of suitable solid carriers are kaolin, talcum, bole, loess, chalk, limestone, ground limestone, dolomite, diatomaceous earth, precipitated silicic acid, alkaline earth silicates (feldspar and mica), calcium and magnesium sulfates, ground synthetic plastics, such as ammonium sulfate, ammonium phosphates, ammonium nitrate, ureas, ground vegetable products such as bran, bark dust, sawdust, ground nutshells, cellulose powder, residues of plant extractions, active charcoal, etc. These carriers can be used alone or admixed with each other.

The particle size of the carrier is, for dusts advantageously up to about 0.1 mm, for scattering agents from about 0.075 to 0.2 mm, and for granulates 0.2 mm or more.

The concentrations of active substance in the solid preparations are from 0.5 to 80%.

To these mixtures can also be added additives which stabilize the active substance and/or non-ionic, anionic and cationic surface active substances which, for exam- Table II

| active substance Example No. | Cont. kg/ha | crop | | | | | weeds/wild graves | | | | | | | |
|---|---|---|---|---|---|---|---|---|---|---|---|---|---|---|
| | | rice dry | rice in water | wheat | soya bean | cotton | lolium multifl. | Setaria ital | echinochloa crus calli | | poa triv. | alope-curus myos. | digita-ria sar-quin. | amaran-thus spez. |
| | | | | | | | | | dry | in water | | | | |
| 1 | 4 | 7 | 8 | — | — | 7 | 2 | 3 | 1 | 2 | 1 | 1 | — | — |
| | 2 | 8 | 9 | — | — | 9 | 2 | 4 | 2 | 4 | 1 | 1 | — | — |
| | 1 | 9 | 9 | — | — | 9 | 2 | 5 | 3 | 7 | 1 | 2 | — | — |
| A* | 4 | 6 | 7 | — | — | — | — | — | 2 | 1 | — | — | — | — |
| | 2 | 6 | 8 | — | — | — | — | — | 4 | 4 | — | — | — | — |
| | 1 | 9 | 9 | — | — | — | — | — | 9 | 9 | — | — | — | — |
| B* | 4 | 9 | 9 | 9 | 4 | 8 | 3 | 3 | 1 | 1 | 8 | 3 | 3 | 9 |
| | 2 | 9 | 9 | 9 | 9 | 9 | 7 | 8 | 2 | 7 | 8 | 8 | 7 | 9 |
| | 1 | 9 | 9 | 9 | 9 | 9 | 7 | 9 | 4 | 9 | 9 | 9 | 9 | 9 |
| C* | 4 | 9 | 9 | 9 | 9 | 9 | 3 | 3 | 3 | 1 | 4 | 6 | 2 | 4 |
| | 2 | 9 | 9 | 9 | 9 | 9 | 9 | 4 | 6 | 7 | 8 | 6 | 3 | 6 |
| | 1 | 9 | 9 | 9 | 9 | 9 | 9 | 9 | 7 | 9 | 9 | 9 | 9 | 9 |

A* 1-(ethylthio-carbonyl)-hexamethyleneimine (known from U.S. Pat. No. 3,198,786)
B* 1-(isopropylthio-carbonyl)-hexamethyleneimine (known from U.S. Pat. No. 3,198,786)
C* 3-(ethylthio-carbonyl)-3-azabicyclo-[3.2.2]-nonane (known from U.S. Pat. No. 3,344,134)

ple, improve the adhesion of the active ingredients on plants or parts of plants (adhesive and agglutinants) and/or ensure a better wettability (wetting agents) and dispersibility (dispersing agents). Examples of suitable adhesives are the following: olein/chalk mixture, cellulose derivatives (methyl cellulose), hydroxyethyl glycol ethers of monoalkyl and dialkyl phenols having 1 to 15 ethylene oxide radicals per molecule and 8 to 9 carbon atoms in the alkyl moiety, lignin sulfonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide, propylene oxide, polyvinyl pyrrolidones, polyvinyl alcohols, condensation products of urea and formaldehyde, and also latex products.

The water-dispersible concentrates of the active substance, i.e. wettable powders, pastes and emulsion concentrates, are compositions which can be diluted with water to any concentration desired. They consist of active substance, carrier, optionally additives which stabilize the active substance, surface-active substances and anti-foam agents and, optionally, solvents. The concentration of active substance in these compositions is 5 to 80 %.

Wettable powders and pastes are obtained by mixing and grinding the active substances with dispersing agents and pulverulent carriers in suitable apparatus until homogeneity is attained. Carriers are, for example, those mentioned for the solid forms of application. In some cases it is advantageous to use mixtures of different carriers. As dispersing agents there can be used, for example, condensation products of sulfonated naphthalene and sulfonated naphthalene derivatives with formaldehyde, condensation products of naphthalene or naphthalene sulfonic acids with phenol and formaldehyde, as well as alkali, ammonium and alkaline earth metal salts of lignin sulfonic acid, in addition, alkylaryl sulfonates, alkali and alkaline earth metal salts of dibutyl naphthalene sulfonic acid, fatty alcohol sulfates such as salts of sulfated hexadecanols, heptadecanols, octadecanols, and salts of sulfated fatty alcohol glycol ethers, the sodium salt of oleoyl ethionate, the sodium salt of oleoyl methyl tauride, ditertiary acetylene glycols, dialkyl dilauryl ammonium chloride and fatty acid alkali and alkaline earth metal salts.

Suitable anti-foam agents are silicones.

The active substances are so mixed, ground, sieved and strained with the additives mentioned above that, in wettable powders, the solid particle size of from 0.02 to 0.04 and in pastes, of 0.03 is not exceeded. To produce emulsion concentrates and pastes, dispersing agents such as those given in the previous paragraphs, organic solvents and water are used. Examples of suitable solvents are the following: alcohols, benzene, xylenes, toluene, dimethyl sulfoxide, and mineral oil fractions boiling between 120° and 350° C. The solvents must be practically odorless, not phytotoxic, inert to the active substances and not readily inflammable.

Furthermore, the compositions according to the invention can be applied in the form of solutions. For this purpose the active substance or several active substances of general Formula I are dissolved in suitable organic solvents, mixtures of solvents or in water. Aliphatic and aromatic hydrocarbons, chlorinated derivatives thereof, alkyl naphthalenes and mineral oils, alone or mixed with each other, can be used as organic solvents. The solution should contain the active substances in a concentration of from 1 to 20%.

The compositions according to the invention can be mixed with other biocidally active compounds or agents. Thus, to broaden the range of action, the new compositions can contain, e.g. insecticides, fungicides, bactericides, fungistatics, bacteriostatics or nematocides in addition to the compounds mentioned of the Formula I. The compositions according to the invention can also contain plant fertilizers, trace elements, etc.

The following non-limitative examples illustrate the preparation of application forms of the new substituted 2-azabicycloalkanes. "Parts" mean parts by weight.

GRANULATE

The following ingredients are used to produce a 5% granulate:

5 parts of 1-(n-propylthio-carbonyl)-2-methyl-decahydro-quinoline.
0.25 part of epichlorohydrin
0.25 part of cetyl polyglycol ether,
3.50 parts of polyethylene glycol ("Carbowax")
91 parts of kaolin (particle size 0.3 – 0.8 mm).

The active ingredient is mixed with epichlorohydrin and dissolved with 6 parts of acetone, then the polyethylene glycol and cetyl polyglycol ether are added. The resulting solution is sprayed onto kaolin and the acetone is then evaporated in vacuo. Similar granulates are obtained on using instead of the above mentioned active substance, e. g. 1-(ethylthio-carbonyl)-2-methyl-decahydro-quinoline.

WETTABLE POWDER

The following components are used for the preparation of (a) 50%, (b) 25% and (c) 10% wettable powders:

a.

50 parts of 1-n-propylthio-carbonyl)-2-methyl-decahydroquinoline,
5 parts of sodium dibutylnaphthyl sulfonate,
3 parts of naphthalene sulfonic acid/phenol sulfonic acid/formaldehyde condensation product 3:2:1,
20 parts of kaolin,
22 parts of Champagne chalk;

b.

25 parts of 1-(n-propylthio-carbonyl)-8-methyl-decahydroquinoline,
5 parts of the sodium salt of oleylmethyl tauride,
2.5 parts of naphthalene sulfonic acid/formaldehyde condensation product,
0.5 part of carboxymethyl cellulose,
5 parts of neutral potassium aluminum silicate,
62 parts of kaolin;

c.

10 parts of 1-(n-propylthio-carbonyl)-2-methyl-decahydroquinoline,
3 parts of mixture of sodium salts of saturated fatty alcohol sulfates,
5 parts of naphthalene sulfonic acid/formaldehyde condensation product,
82 parts of kaolin.

The given active ingredient is absorbed onto the corresponding carriers (kaolin and chalk) and then mixed and ground. Wettable powders having excellent wettability and suspensibility are obtained. By dilution with water, suspensions of any desired concentration of the active ingredients can be obtained from such wettable powders.

Such suspensions are suitable for the control of weeds and wild grasses in water and dry cultivations of rice before and after emergence of the rice plants.

Similar wettable powders are obtained when instead of the above mentioned active substances, e.g. 1-(ethylthio-carbonyl)-2-methyl-decahydro-quinoline, 1-(methylthio-carbonyl)-2-methyl-decahydro-quinoline are used.

PASTE

The following ingredients are used for the preparation of a 45% paste:

45 parts of 1-(n-propylthio-carbonyl)-2-methyl-decahydroquinoline, 5 parts of sodium aluminum silicate, 14 parts of cetyl polyglycol ether having 8 mol of ethylene oxide, 1 part of cetyl polyglycol ether having 5 mol of ethylene oxide, 2 parts of spindle oil, 10 parts of polyethylene glycol, 23 parts of water.

The active ingredient is intimately mixed and ground in suitable equipment with the additives. A paste is obtained which can be diluted with water to prepare suspensions of any desired concentration. The suspensions are suitable, for example, for the treatment of water cultivations of rice before and after emergence of the cultivated plants.

EMULSION CONCENTRATE

To prepare a 10% emulsion concentrate 10 parts of 1-(n-propylthio-carbonyl)-2-methyl-decahydroquinoline 15 parts of oleyl polyglycol ether having 8 mol of ethylene oxide, and 75 parts of isophorone are mixed together. This concentrate can be diluted with water to emulsions of suitable concentrations. Such emulsions are applied, for example, before the emergence of the rice plants in dry cultivations thereof.

Similar emulsion concentrates are obtained when, instead of the above mentioned active substance, e.g.

1-(ethylthio-carbonyl)-2-methyl-decahydro-quinoline is used.

What we claim is:

1. A selective herbicidal composition which comprises a herbicidally effective amount of a compound of the formula

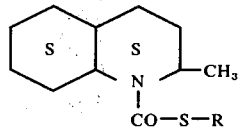

wherein R is ethyl, n-propyl or isopropyl, together with an agriculturally acceptable carrier therefor.

2. A composition according to claim 1, which comprises as active substance 1-(n-propylthio-carbonyl)-2-methyl-decahydroquinoline of the formula

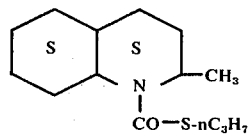

3. A method for selectively controlling weeds and wild grasses in rice crops which comprises applying to the crop areas intended for rice cultivating a herbicidally effective amount of a compound according to claim 1.

4. A method according to claim 3 which comprises applying a herbicidally effective amount of the compound 1-(n-propylthiocarbonyl)-2-methyl-decahydroquinoline of the formula

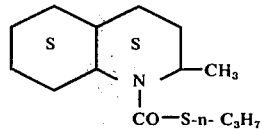

5. The method of claim 3, wherein said compound is 1-(ethylthio-carbonyl)-2-methyl-decahydroquinoline.

6. The method of claim 3, wherein said compound is 1-(iso-propylthio-carbonyl)-2-methyl-decahydroquinoline.

* * * * *